United States Patent
Van Der Meyden et al.

[11] Patent Number: 6,080,131
[45] Date of Patent: Jun. 27, 2000

[54] VIAL FOR USE AS SYRINGE ACCESSORY

[75] Inventors: Hendrikus J Van Der Meyden, Midrand; Alexis A. F. Wadman, Bedfordview, both of South Africa

[73] Assignee: Nordway Limited, United Kingdom

[21] Appl. No.: 09/180,229

[22] PCT Filed: May 6, 1997

[86] PCT No.: PCT/GB97/01231

§ 371 Date: Nov. 3, 1998

§ 102(e) Date: Nov. 3, 1998

[87] PCT Pub. No.: WO97/41909

PCT Pub. Date: Nov. 13, 1997

[30] Foreign Application Priority Data

May 3, 1996 [ZA] South Africa ............................ 96/3500

[51] Int. Cl.$^7$ .................................................. A61M 37/00
[52] U.S. Cl. ................................ 604/82; 604/90; 206/221
[58] Field of Search ................................ 604/89, 90, 232, 604/237, 238, 92, 82, 181, 191, 218, 221, 236; 206/219, 221

[56] References Cited

U.S. PATENT DOCUMENTS

| | | |
|---|---|---|
| 2,567,001 | 9/1951 | Watson . |
| 2,604,095 | 7/1952 | Brody . |
| 5,290,228 | 3/1994 | Uemura et al. ............................ 604/90 |
| 5,335,773 | 8/1994 | Haber et al. ............................ 206/221 |
| 5,599,312 | 2/1997 | Higashikawa ............................ 604/191 |
| 5,685,846 | 11/1997 | Michaels, Jr. ............................ 604/90 |

FOREIGN PATENT DOCUMENTS

| | | |
|---|---|---|
| 0 112 574 A1 | 7/1984 | European Pat. Off. . |
| 0 695 555 A1 | 2/1996 | European Pat. Off. . |

*Primary Examiner*—Mark O. Polutta
*Assistant Examiner*—Kelly M Cheney
*Attorney, Agent, or Firm*—Knobbe, Martens, Olson & Bear LLP

[57] ABSTRACT

A vial comprises a tubular syringe barrel (1) closed at one end (2) and open at the other, a stopper in the open barrel end formed by a piston head (4) of a syringe, and valve means (10) in the barrel between the stopper and the closed barrel end. The valve means (1) is normally closed and actuatable to an open condition by movement of the stopper into the barrel, and is slidable with the piston head (4) to the closed barrel end (2).

14 Claims, 2 Drawing Sheets

VIAL FOR USE AS SYRINGE ACCESSORY

FIELD OF THE INVENTION

This invention relates to a vial for holding drugs, and mixtures which can optionally serve as a syringe accessory.

BACKGROUND TO THE INVENTION

It is known to use a syringe barrel as a prepackaged container for drugs. The barrels in these cases are of the type which are moved relative to a piston which has a fluid pathway through it. The barrels normally have one opening which has a removable seal, and after unsealing, the open end is located over a piston head for use.

OBJECT OF THE INVENTION

It is an object of this invention to provide a vial of the type described above.

SUMMARY OF THE INVENTION

In accordance with this invention there is provided a vial comprising a tubular syringe barrel closed at one end and open at the other, a stopper in the open barrel end formed by a piston head of a syringe, and valve means in the barrel between the stopper and the closed barrel end, the valve means being normally closed and actuatable to an open condition by movement of the stopper into the barrel, and the valve means being slidable with the piston head to the closed barrel end.

Preferably, the valve means is actuatable by hydraulic pressure from a liquid being operated on by the stopper when pressed into the barrel.

There is provided for the valve means to have a body which is slidable within a sealing surround, with the body having openings in it and being slidable from a closed position in which the openings are sealed by the sealing surround, to an open position where the openings in the body move passed the sealing surround.

Preferably, the body is a blind ended tube with an outwardly extending annular skirt located at the open tube end, the tube having radial openings between the skirt and the blind end, and an annular seal around the blind end.

The seal may alternatively extend axially from the blind end, spaced from and around the tube, to seal around the skirt.

BRIEF DESCRIPTION OF THE DRAWING

Preferred embodiments of the invention are described below by way of example only, and with reference to the accompanying drawings, in which.

DETAILED DESCRIPTION OF THE DRAWINGS WITH REFERENCE TO THE DRAWING

Figure 1:
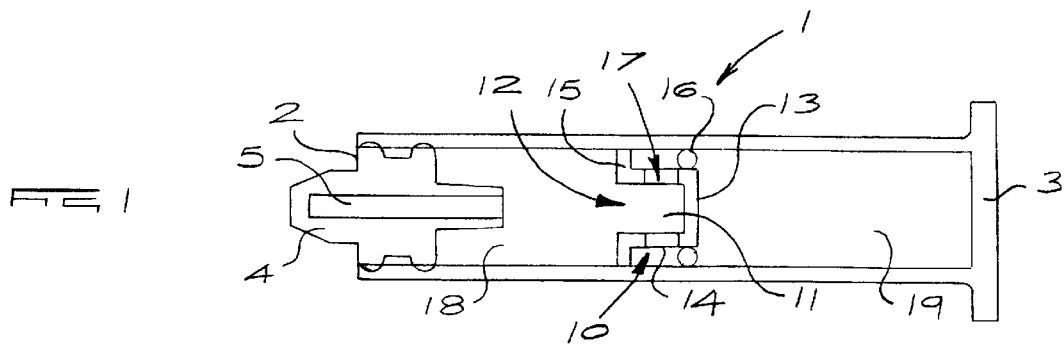
FIGS. 1 to 3 are cross-sectional side views of a first embodiment of the invention in stages of use; and, FIGS. 4 to 5 are cross-sectional side views of a second embodiment of the invention in stages of use.
Figure 2:
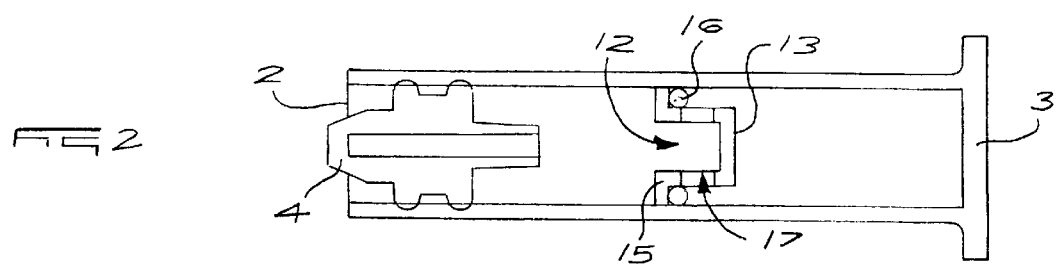
Figure 3:
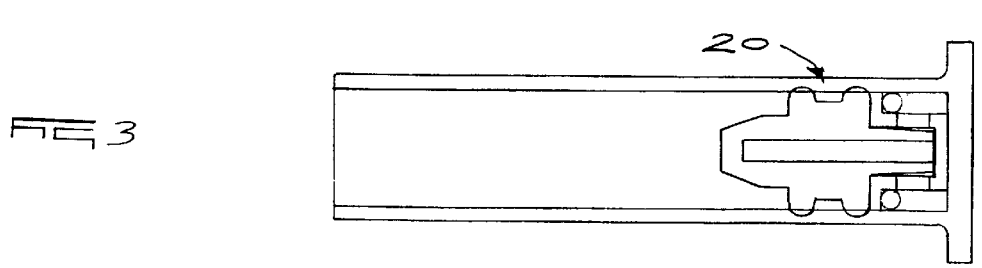

Referring to FIGS. 1 to 3, a syringe barrel (1) is tubular with an open end (2) and a closed end (3). The barrel has a piston head (4) located in the open end, operating as a stopper. The piston head (4) has a blind passageway (5) formed therein running from the interior piston end where it is open, to the blind end facing out of the barrel, at the external end of the piston. As will be appreciated by those who are skilled in the art, this piston is pressed in use into the sharp end of a needle passageway as part of a syringe. The blind end of the piston passageway is pierced to create a path for liquid to be discharged.

A valve means (10) is located in the barrel between the piston head (4) and the closed end (3). The valve means divides the barrel interior into a chamber (18) nearest the piston head, and a chamber (19) nearest the closed end (3). The chamber (18) is filled with a liquid component, and the chamber (19) is filled with a granular or powder component in a form that is at least partially compressible, or which does not completely fill the chamber (19). Normally, the liquid is a sterile solution which must be mixed with a powdered drug, normally an antibiotic.

The valve means (10) has a body (11) in the form of a short blind ended tube, having an open end (12) leading to the blind end (13). The wall (14) of the tube is spaced away from the barrel walls, and at the open end a radially outwardly extending skirt (15) provides a sliding fit for the valve means body within the barrel interior. At the blind end (13) is located sealing means (16) in the form of an O-ring. The O-ring locates in a sealing manner around the blind end (13). Radial openings (17) are located in the wall (14) between the skirt (15) and the installed position of the O-ring.

In use, the piston head (4) is pressed into the barrel and the compression force on the liquid in the chamber (18) forces the valve means towards the second chamber (19), and passed the O-ring (16). The O-ring has sufficient frictional engagement with the interior of the barrel to cause it to roll past the openings (17), thus connecting the two chambers through the radial openings (17). This position is shown in FIG. 2.

The barrel can now be shaken up gently to ensure that the liquid and solid components are properly mixed. The barrel is then connected with the syringe as described above, and the contents injected. During the course of injection the piston head moves to the rear interior of the barrel and in doing so engages the body (11). The body (11) is slid together with the piston head to abut the interior of the closed end (3) of the barrel, as indicated by numeral (20) in FIG. 3.

Figure 4:
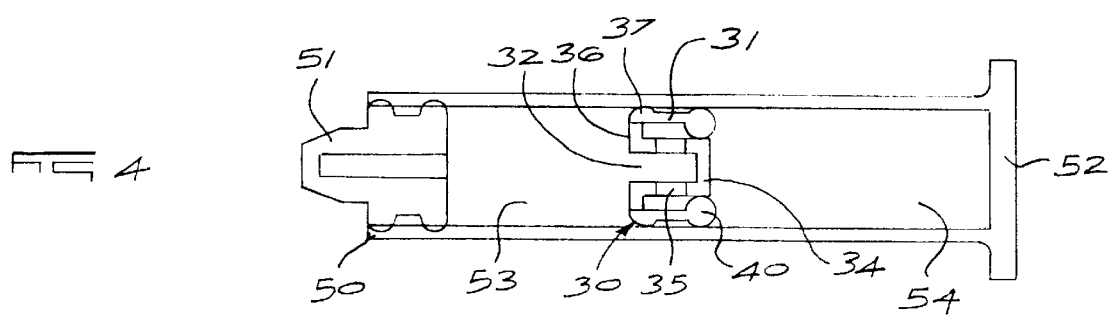
Figure 5:
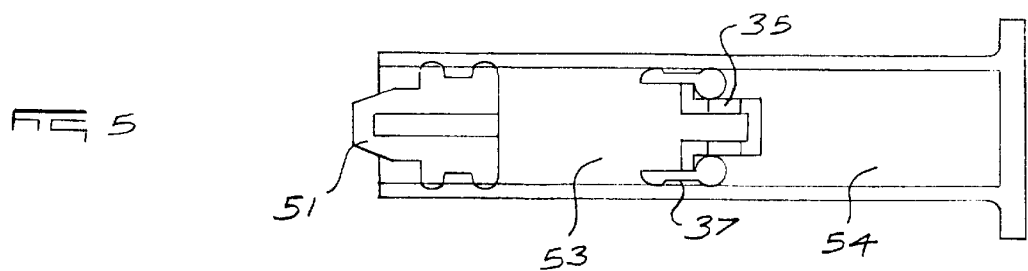

Referring now to FIGS. 4 to 5, an alternative embodiment of a valve means is shown. In this embodiment a valve means (30) has a sealing surround (31) in the form of a band of sealing material which locates around and extends between an open end (32) and a closed end (33) of a valve body (34). The valve body is similar in configuration to that described with reference to FIGS. 1 to 3, having openings (35) in the walls of a short blind ended tube, and a radially outwardly extending skirt (36) around the open tube end (32). The skirt however does not abut the barrel interior but locates against one axial end (37) of the sealing ring. The opposite axial end (40) of the sealing ring is radially thicker, extending inwardly to locate and seal around the blind end (33) of the body.

The valve means is fitted within a syringe barrel (50) having a piston head (51) closing the open end thereof, and having an opposite closed end (52). The valve means divides the barrel into two chambers, being a chamber (53), normally filled with liquid and located between the valve means and the piston head (51), and a chamber (54) between the valve means and the closed end (53). The chamber (54) is normally provided with a solid material for mixing with the liquid in chamber (53).

In use, the piston head (51) is pressed into the barrel causing the liquid in the chamber (53) to action the valve body and slide it into the chamber (54) and passed the sealing means (37). In this position the radial openings (35) move passed the sealing means and allow the two chambers to communicate with each other.

As described above with reference to FIGS. 1 to 3, the barrel is now shaken up to mix the contents of the two chambers and connected to a syringe for discharge.

Variations may be made to the above embodiments without departing from the scope of the invention. A removable plug may be located over the piston head to keep the head sterile prior to mixing, and the piston may be replaced by a movable stopper.

What is claimed is:

1. An apparatus comprising a tubular syringe barrel, an end wall forming one end of the barrel, the other end of the barrel being an open end, a stopper in the open barrel end, and a valve arranged in the barrel between the stopper and the end wall so as to impermeably divide the barrel into a first chamber extending from the stopper to the valve and a second chamber extending from the end wall to the valve, the valve being normally in a closed position and actuatable to an open position by movement of the stopper into the barrel to allow communication between the first and second chambers, wherein the valve comprises an annular sealing surround engaged with an interior surface of the barrel and a tubular body slidably engaged within the annular sealing, the tubular body has an open end toward the first chamber, a blind end toward the second chamber, and an opening on a side between the blind end and the open end thereof, wherein in the closed position of the valve, the annular sealing surround is located near the blind end of the tubular body, and wherein in the open position of the valve, the annular sealing surround is located near the open end of the tubular body.

2. An apparatus as defined in claim 1, wherein at least one of the first and second chambers contains powder.

3. An apparatus as defined in claim 1, wherein the valve is slidably arranged in the barrel so that the valve moves along the barrel with the stopper.

4. An apparatus as defined in claim 1, wherein the valve is actuated such that when the stopper is pressed into the barrel, the tubular body slides within the annular sealing surround toward the end wall and the opening of the tubular body allows the fluid communication between the first and second chambers.

5. A method for actuating the valve of the apparatus as defined in claim 1, comprising pressing the stopper into the barrel.

6. An apparatus according to claim 1, wherein the tubular body further comprises an outwardly extending annular skirt located at the open end, and wherein the annular sealing surround is proximate to the skirt when in the open position.

7. An apparatus according to claim 6, wherein the annular sealing surround extends axially from the blind end, spaced from and around the tube, to form a seal around the skirt between the skirt and the barrel.

8. An apparatus as defined in claim 6, wherein the first chamber contains liquid.

9. An apparatus according to claim 8, wherein the valve is actuatable by hydraulic pressure of the liquid contained in the first chamber operated by the stopper when pressed into the barrel.

10. A method for providing a vial, comprising:

providing a tubular syringe barrel having a closed end and an open end;

providing a valve comprising an annular sealing surround and a tubular body slidably engaged within the annular sealing, wherein the tubular body has an open end, a blind end and an opening on a side between the blind end and the open end thereof, filling a first material within a first chamber defined from the closed end to a level of the barrel;

engaging the valve in the barrel at the level, thereby dividing the barrel into the first chamber defined from the valve to the closed end of the barrel and a second chamber defined from the valve to the open end of the barrel wherein the annular sealing surround is engaged with an interior surface of the barrel, and wherein the open end of the tubular body is toward the first chamber and the blind end of the tubular body is toward the second chamber;

filling a second material within the second chamber; and closing the open end of the barrel the with a stopper to be slidably pressed into the barrel;

wherein the valve being normally in a closed position and actuatable to an open position by movement of the stopper into the barrel to allow communication between the first and second chambers, wherein in the closed position of the valve, the annular sealing surround is located near the blind end of the tubular body, and wherein in the open position of the valve, the annular sealing surround is located near the open end of the tubular body.

11. The method as defined in claim 10, wherein at least one of the first and second materials is in powder.

12. The method as defined in claim 11, wherein the valve is actuatable by hydraulic pressure of the liquid contained in the first chamber operated by the stopper when pressed into the barrel.

13. The method as defined in claim 10, wherein the first and second materials comprises drug.

14. The method as defined in claim 10, wherein the first material is in liquid phase.

* * * * *